(12) United States Patent
Stenfeldt et al.

(10) Patent No.: US 11,607,463 B2
(45) Date of Patent: Mar. 21, 2023

(54) DIAGNOSTIC USAGES OF SHORT-LIVED RADIOPHARMACEUTICALS

(71) Applicant: MedTrace Pharma A/S, Kongens Lyngby (DK)

(72) Inventors: Martin Stenfeldt, Vedbæk (DK); Rune Wiik Kristensen, Hinnerup (DK); Peter Larsen, Værløse (DK)

(73) Assignee: MedTrace Pharma A/S, Kongens Lyngby (DK)

( * ) Notice: Subject to any disclaimer, the term of this patent is extended or adjusted under 35 U.S.C. 154(b) by 124 days.

(21) Appl. No.: 17/132,014

(22) Filed: Dec. 23, 2020

(65) Prior Publication Data

US 2021/0187129 A1 Jun. 24, 2021

Related U.S. Application Data

(62) Division of application No. 16/472,100, filed as application No. PCT/EP2017/084128 on Dec. 21, 2017, now Pat. No. 11,285,225.

(30) Foreign Application Priority Data

Dec. 21, 2016 (EP) .................... 16205724

(51) Int. Cl.
  *A61K 51/02* (2006.01)
  *A61M 5/168* (2006.01)

(52) U.S. Cl.
  CPC ....... *A61K 51/025* (2013.01); *A61M 5/16831* (2013.01); *A61M 5/16881* (2013.01); *A61M 2205/3341* (2013.01); *A61M 2205/3379* (2013.01)

(58) Field of Classification Search
  None
  See application file for complete search history.

(56) References Cited

FOREIGN PATENT DOCUMENTS

| EP | 2457602 A1 | 5/2012 |
|---|---|---|
| EP | 3106200 A1 | 12/2016 |

OTHER PUBLICATIONS

International Search Report and Written Opinion for International Application No. PCT/EP2017/084128 dated Apr. 5, 2018 (12 pages).
Kellner, E. et al., "Quantitative Cerebral Blood Flow with Bolus TrackingPerfusion MRI: Measurements in Porcine Model and Comparison with H152 O PET" 2014 Magnetic Resonance in Medicine 72:1723-1734.
Kuwabara, Y. et al., "Cerebral blood flow and vasodilatory capacity in anemia secondary to chronic renal failure" 2002 Kidney Intl 61:2:564-569.
Lee et al. "Test-retest reproducibility of [11 C]-(+)-propyl-hexahydro-naphtho-oxazin positron emission tomography using the bolus plus constant infusion paradigm." 2013 Mol. Imaging 12: 77-82. Author manuscript, 11 p. (Year: 2013).
Tiwari, V.N., et al., "Automatic labeling method for injectable 15O-oxygen using hemoglobin-containing liposome Vesicles and its application for measurement of brain oxygen consumption by PET" 2010 Nuclear Medicine and Biology 37:77-83.
Van Der Veldt, A.A.M., et al. "Quantitative Parametric Perfusion Images Using 15O-Labeled Water and a Clinical PET/CT Scanner: Test-Retest Variability in Lung Cancer" 2010 J Nucl Med; 51:1684-1690.
Restriction Requirement for U.S. Appl. No. 16/472,100, dated Sep. 24, 2020. 8 pages.

*Primary Examiner* — Jennifer Lamberski
(74) *Attorney, Agent, or Firm* — Quarles & Brady LLP

(57) ABSTRACT

The present invention relates to the use of radiopharmaceuticals having a radioactive half-life of less than 21 minutes, such as oxygen-15 labeled water ($H_2^{15}O$) in blood flow imaging using PET (Positron emission tomography) scanning technology. The invention also relates to the use of a system for preparing and injecting boluses of such radiopharmaceuticals.

6 Claims, 11 Drawing Sheets

DIAGNOSTIC USAGES OF SHORT-LIVED RADIOPHARMACEUTICALS

CROSS REFERENCE TO RELATED APPLICATION

This patent application is a divisional of U.S. patent application Ser. No. 16/472,100, filed Jun. 20, 2019, which is a national stage filing under 35 U.S.C. 371 of International Application PCT/EP2017/084128, filed Dec. 21, 2017, which claims the benefit of priority to European Patent Application No. 16205724.4, filed Dec. 21, 2016, all of which are incorporated herein by reference in their entireties.

FIELD

The present invention relates to the use of radiopharmaceuticals having a radioactive half-life of less than 21 minutes, such as oxygen-15 labeled water ($H_2^{15}O$) in blood flow imaging using PET (Positron emission tomography) scanning technology. The invention also relates to the use of a system for preparing and injecting boluses of such radiopharmaceuticals.

BACKGROUND

Nuclear medicine is a rapidly growing branch of medicine that uses radiation to provide diagnostic information about the functioning of a person's specific organs or to use the radiation to treat disease, for example intravenous radiation therapy within the field of oncology. In most cases, the information is used by physicians to make a quick, accurate diagnosis of the patient's illness. Organs such as the thyroid, bones, heart, liver, brain and many other can be easily imaged, and disorders in their function revealed. In some cases, radiation can be used not only for diagnostic purposes but also to treat diseased organs, or tumours.

Over 10,000 hospitals worldwide use radioisotopes in medicine, and about 90% of the procedures are for diagnosis.

In developed countries (26% of world population) the frequency of diagnostic nuclear medicine is 1.9% per year, and the frequency of therapy with radioisotopes is about one tenth of this. In the USA there are over 20 million nuclear medicine procedures per year among 311 million people, and in Europe about 10 million among 500 million people. In Australia there are about 560,000 per year among 21 million people, 470,000 of these using reactor isotopes. The use of radiopharmaceuticals in diagnosis is growing at over 10% per year ("Radioisotopes in Medicine", World Nuclear Association November 2016).

Single Photon Emission Computed Tomography (SPECT) scan was the first type of nuclear imaging test capable of showing how blood flows to tissues and organs. The radioisotopes typically used in SPECT to label tracers typically have half-lives on the order of several hours to days, eg. iodine-123 (Half-Life: app. 13 hours), technetium-99m (Half-Life: app. 6 hours), xenon-133 (Half-Life: app. 5 days), thallium-201 (Half-Life: app. 73 hours), and fluorine-18 (Half-Life: app. 2 hours).

Positron emission tomography (PET) scan has increasingly become an important diagnostic tool for assessing blood flow and organ and tissue perfusion. Radioisotopes such as $^{18}F$, $^{11}C$, $^{15}O$, $^{82}Rb$ and $^{13}N$ are typically used in labelling radiopharmaceuticals for use with PET. The half-life associated with these radioisotopes is very short, typically on the order of minutes (except $^{18}F$ (F-18) which has a half-life of almost two hours). Oxygen-15 ($^{15}O$ or O-15) has a half-life of 122.24 seconds and is one of the most suitable radioactive isotopes for use in PET (Positron emission tomography) for quantifying regional cerebral blood flow (rCBF), and for quantifying regional myocardial blood flow (rMBF).

Oxygen-15 labeled $H_2O$ ($H_2^{15}O$, in the following referred to as "O-15 H2O") is indeed broadly recognized as the gold standard for perfusion imaging for all organs, but the drug has only achieved limited use in research applications and drug development programs thus far, due to manufacturing and regulatory challenges arising from the short half-life of only 122 seconds. The short half-life necessitates a system that both produces and injects radioisotopes directly into the patient for it to have broad clinical utility. Therefore, $^{15}O$ is only used to a limited extent in for example research purposes or under special waivers.

A key aspect of the safety considerations in a system that both produces and injects radiopharmaceuticals based on gaseous radioisotopes into patients, is the presence of compressed gas. A cyclotron is connected to one end of such systems which delivers compressed radioactive gas pressurized to 10 bar or more. At the other end of the system a patient is connected, often through a peripheral venous catheter, establishing a potentially direct connection between the patient and the compressed radioactive gas.

Standard safety features typically consist of the gas passing on one side of a semipermeable membrane and saline passing on the other side. Immediately before the patient a sterile filter made of a similar material as the first semipermeable membrane will be located. The sterile filter will gas-lock in the event that any gas passes through the first membrane, but if a gas waste tube leading the gas away is blocked, the pressure may rise to a higher pressure than the membrane can handle, which may allow the gas to pass through both filters and into the patient. The result could be the infusion of radioactive gas into the patient from several hundred ml/minute up to 1-2 l/minute, which may cause fatal venal air embolisms.

Another important issue is the question of accurate dosing of O-15 H2O. Dosing of pharmaceuticals for I.V. injection in hospital or clinical environments is typically done volumetrically from a parent solution having a known concentration. This methodology cannot be used within the field of radiopharmaceuticals, however, due to their radioactive nature.

For radiopharmaceuticals, the effective concentration in the parent solution will decrease constantly at an exponential rate proportional to the decay constant of the radioactive isotope (or isotopes) intrinsic in the pharmaceutical.

For this reason, the way radiopharmaceuticals are dosed today is by measuring the radioactivity in Bequerel or Curie, and timing the point of injection with the desired dose to the patient. In this fashion an excess dose is withdrawn from a parent solution undergoing exponential radioactive decay of the radiopharmaceutical. The withdrawn dose is measured and recorded with a time stamp. When the dose reaches the predetermined activity threshold level, the dose is injected into the patient. For short-lived radioisotopes such as $^{15}O$, this procedure is not practical.

Therefore, in order to use O-15 H2O as a flow and perfusion marker, it has to be provided by a system that both produces and injects O-15 H2O directly into the patient, and the dose has to be uniform in both volume and activity in order for it to be:

comparable between patient cohorts, and reproducible in the same patient.

Furthermore, the dose has to be homogeneous with an even distribution of (radio)activity across the entire dose volume. Finally, the system should be sufficiently fast and efficient to be capable of producing radioactive solutions with high radioactivity concentration such that the volume of injected doses can be kept low.

A therapeutic area where easier access to O-15 H2O based PET scanning is considered highly important is the field of oncology. Within oncology, tumor hypoxia is a distinct state where tumor cells have been deprived of oxygen. As a tumor grows, it rapidly outgrows its blood supply, leaving portions of the tumor with regions where the oxygen concentration is significantly lower than in healthy tissues.

Hypoxic microenvironments in solid tumors are a result of available oxygen being consumed within 70 to 150 μm of tumor vasculature by rapidly proliferating tumor cells thus limiting the amount of oxygen available to diffuse further into the tumor tissue.

Poorly formed tumor blood vessels cause a bottleneck that limits oxygen supply to the growing tumor [Vaupel P. Tumor microenvironmental physiology and its implications for radiation oncology. Semin Radiat Oncol. 2004; 14:198-206], [Secomb T W, Hsu R, Braun R D, Ross J R, Gross J F, et al. Theoretical simulation of oxygen transport to tumors by three-dimensional networks of microvessels. Adv Exp Med Biol. 1998; 454:629-634]. Oxygen consumption within the tumor causes an imbalance with delivery resulting in hypoxia and its sequella [Secomb T W, Hsu R, Ong E T, Gross J F, Dewhirst M W. Analysis of the effects of oxygen supply and demand on hypoxic fraction in tumors. Acta Oncol. 1995; 34:313-316]. Hypoxia has been shown to have many effects on tumor cells, the severity of the response is dependent on the level of oxygen deprivation [Hockel M, Vaupel P. Tumor hypoxia: definitions and current clinical, biologic, and molecular aspects. J Natl Cancer Inst. 2001; 93:266-276], [Papandreou I, Krishna C, Kaper F, Cai D, Giaccia A J, et al. Anoxia is necessary for tumor cell toxicity caused by a low-oxygen environment. Cancer Res. 2005; 65:3171-3178]. With respect to tumor growth characteristics, moderate hypoxia causes a slowing of tumor cell proliferation, while severe hypoxia causes outright cell death [Papandreou I, Krishna C, Kaper F, Cai D, Giaccia A J, et al. Anoxia is necessary for tumor cell toxicity caused by a low-oxygen environment. Cancer Res. 2005; 65:3171-3178], [Santore M T, McClintock D S, Lee V Y, Budinger G R, Chandel N S. Anoxia-induced apoptosis occurs through a mitochondria-dependent pathway in lung epithelial cells. Am J Physiol Lung Cell Mol Physiol. 2002; 282: L727-734].

The hypoxic area of a tumor is therefore difficult to treat, since the slow growth means a reduced cell division frequency. The reduced frequency means for instance that in radiation therapy where tumor cell death is obtained through DNA damage in the cell, the "kill effect" is reduced in hypoxic tumor areas compared to other, more rapidly growing parts of the tumor because the slow growth of cells in hypoxic areas also means that the tumorigenic cells in these areas have lower exposure of their DNA in the prometaphase, metaphase and anaphase of the cell cycle.

In intravenously administered therapy, such as chemotherapy, hypoxic tumor areas are also much more difficult to treat than more rapidly growing parts of the tumor, because of the poor vascularisation of hypoxic tumor areas. The relative dose of the delivered therapeutic agent to the area/volume of interest is significantly reduced in hypoxic tumor areas compared to areas of normal blood supply. The reduced blood flow to hypoxic areas is thus believed to be a key factor as to why drug treatment of hypoxic tumors is very difficult. It is particularly difficult to establish the exact location of the hypoxic area and moreover the state or degree of hypoxia in a given tumor area for a given patient. A high patient variation is experienced, even for the same cancer sub-form, and the hypoxic state or degree is not necessarily stable for the individual patient, but may both improve over time (by improved vascularization of the growing tumor) or deteriorate.

Detailed knowledge of the extent of tumor hypoxia would therefore be desirable when planning the treatment of a cancer patient, which in the case of intravenous drug treatment would make it possible to delay such treatment until the hypoxic condition has first been treated.

However, the generalized, underlying problem can be stated as how to diagnose with greater precision (and greater safety for both the patient and medical staff involved) not only oncological diseases such as tumor hypoxia, but a long range of other disease states or medical conditions such as apoplexy including ischemic apoplexy, vascular dementia, renal failure, muscular ischemia, myocardial ischemia, general microvascular disease, vasculitis, pancreatic failure and other conditions related to blood flow impairment.

There thus remains a need for a safe and reliable, non-surgical method which can provide detailed knowledge regarding the blood flow and perfusion of an individual patient's tissue and organs, preferably with high capacity and low operational costs.

Definitions

As used herein, the term "radioactive concentration" of a solution refers to the amount radioactivity per unit volume of the solution, eg per unit volume of an administered bolus of a radiopharmaceutical. The radioactive concentration will be measured in megaBecquerels per millilitre (MBq/ml).

As further used herein, the expression "the radioactivity $A_{act}$ of said bolus differs at most ±10% from a predetermined value $A_{det}$" means that, at the point in time where the bolus is injected, the radioactivity concentration of the bolus (as measured in eg. MBq/ml) shall differ at most ±10% from the predetermined value decided by the operator. If, for example, the desired radioactivity concentration of the bolus is 200 MBq/ml, then the actually delivered bolus by the system of the invention will have a radioactivity concentration in the range of 180-220 MBq/ml.

Additionally, the expression "the radioactivity $A_{act}$ of said bolus differs at most ±10% from a predetermined value $A_{det}$" shall further mean in the context of the present application, that at the point in time where the bolus is injected, the radioactivity (as measured in eg. MBq) contained in the bolus shall differ at most ±10% from the predetermined value decided by the operator. If, for example, the desired radioactivity is 400 MBq, then the actually delivered bolus by the system of the invention will contain a radioactivity of 360-440 MBq. The system according to the present invention can however operate with more narrow limits than ±10% as regards both level of radioactivity and bolus volume. Ranges of ±7%, ±5%, ±2% and even ±1% are possible in most cases.

Since the radioactive concentration will change with time due to decrease in the nuclide radioactivity it is always necessary to provide a reference time. As with all statements involving radioactivity, it is necessary to include a reference date and time of standardization. For radionuclides with a half-life period of less than 21 minutes, a more precise statement of the reference time is required including time of day in addition to date.

As used herein, the term "substantially cylindrical body" refers to a three-dimensional object having a longitudinal axis and a uniform cross section along the longitudinal axis which is preferably circular, ellipsoid or oval, but which may have a cross section of any geometrical shape, including polygonal. Preferably, a substantially cylindrical body as used herein refers to a cylindrically shaped object having a substantially circular cross section.

As used herein, the term "coincidence detection" refers to the simultaneous detection of two gamma ray photons arisen initially from β* decay with positron emission and subsequent electron-positron annihilation. The process in creating the two gamma ray photons conserve electric charge, linear momentum, angular momentum and lepton number during the process: $e^-+e^+\rightarrow\gamma+\gamma$ which allows for the simultaneous detection using appropriate apparatus (coincidence detectors).

SUMMARY OF THE INVENTION

The invention is explained below in terms of oncology, but is generally applicable to other disease states or medical conditions which involves the assessment of blood flow and organ perfusion in an individual patient.

The invention relates to the non-surgical use of a specific, well-defined dose of a radiopharmaceutical having a radioactive half-life of <21 minutes administered to a patient harboring a suspected or known tumor, or for use in the modelling of a human heart, and/or chambers and cavities therein, such as the left and right atrium as disclosed in co-pending international patent application PCT/DK2017/050367, where the dose is given intravenously in such a manner that the patient receives a homogenous bolus of the radiopharmaceutical which is defined with high precision as to volume, radioactivity and injection speed, so that the described parameters of the bolus (being volume, radioactivity and injection speed) satisfy the requirements for a PET scanning of the patient with subsequent computerized analysis of the obtained data by software algorithmic means in order to calculate the blood flow through the suspected or known tumor or target organ.

In this way distinct tumor (and other perfusable organ) characteristics such as volume, weight and local perfusability become inferable in a qualitative way or on a quantitative scale. Furthermore, these distinct characteristics become principal dosing means for qualitative or quantitative treatment planning. By qualitative treatment planning is implied, for example, deselection of a currently established treatment plan for a given oncologic state based upon principally the absence of blood flow to necrotic or hypoxic areas. By quantitative treatment planning is implied, for example, the individual treatment planning including prescribed therapeutic doses based upon the relative quantified blood flow to the necrotic, hypoxic or normal tumor area.

The administered dose (D) dose of a radiopharmaceutical having a radioactive half-life of <21 minutes should be of a size suitable to the detection limit of the scanner, local scanner settings and conditions as well as the individual patients age, weight, sex and ethnicity.

The bolus volume (V) should be of a size to allow for a rapid introduction into the body, and suitable as regards the individual patients age, weight, sex and ethnicity. For different diagnostic purposes (V) will be within the range of 0.05-50 ml. The injection speed (S) should be sufficiently fast to allow for rapid introduction of the volume (V) into the body, and suitable as regards the individual patients age, weight, sex and ethnicity.

The invention thus relates to a bolus for non-surgical, intravenous (IV) administration comprising a liquid solution of a radiopharmaceutical having a radioactive half-life of <21 minutes for use in blood flow imaging, characterized in that said bolus has a substantially cylindrical body or delimitation and an unvarying (homogeneous) radioactivity profile throughout the volume of the bolus.

In a second aspect the invention relates to a bolus as defined in the first aspect of the invention for use in the diagnosis of a disease or medical condition selected from tumor hypoxia, apoplexy including ischemic apoplexy, vascular dementia, renal failure, muscular ischemia, myocardial ischemia, general microvascular disease, vasculitis, pancreatic failure and other conditions related to blood flow impairment, or for use in the modelling of a human heart, and/or chambers and cavities therein, such as the left and right atrium as disclosed in co-pending international patent application PCT/DK2017/050367.

In a third aspect the invention relates to a non-surgical method for preparing and administering a bolus according to the first or second aspect of the present invention, which method comprises:
Providing a source of a liquid solution of a radiopharmaceutical having a radioactive half-life of less than 21 minutes,
providing a first valve having a waste position and a recipient position,
providing a bolus conduit (a), a waste conduit (b) and a recipient conduit (c), each conduit having a valve end being connected to said first valve, so that the first valve can establish a waste flow path in the waste position and a recipient flow path in the recipient position, the recipient flow path being different from said waste flow path, the bolus conduit comprising a measuring section and an internal volume, the internal volume being approximately equal to the selected volume of the radioactive solution to be delivered to the recipient,
arranging said first valve in the waste position,
transporting a first amount of said radioactive solution through said waste flow path, the first amount of said radioactive solution having an initial level of radioactivity that is at least approximately equal to or higher than the selected level of radioactivity and a volume that is larger than the internal volume of said bolus conduit,
providing a radiation detector, the radiation detector being operable to measure a level of radioactivity of the radioactive solution in said measuring section, measuring a reference level of radioactivity of said radioactive solution present in
said measuring section,
characterized in that when the reference level of radioactivity is approximately equal to a predetermined injection level of radioactivity, the method further comprises the steps of:
arranging the first valve in the recipient position, and
transporting the radioactive solution present in the bolus conduit through the recipient flow path.

In a fourth aspect the invention relates to a bolus as defined in the first aspect of the invention for use in radionuclide therapy, wherein the radiopharmaceutical having a radioactive half-life of less than 21 minutes is based on a beta- or alpha-emitting radioisotope, or an Auger electron emitting radioisotope in such a manner that the principal mechanism of action of the radioisotope is to cause harm to the tumor area with a therapeutic effect, but with a secondary aspect being that the first mechanism gives rise to a secondary radiation effect making it possible to image the presence and effect of the isotopes and hereby infer the relative presence and concentration of the isotopes within the field/region of interest.

DESCRIPTION OF DRAWINGS

FIG. 1 shows the Production Kit whereas FIG. 2 shows the Infusion Kit. The two parts are assembled via Connector 7 shown in the top-right corner of the Production Kit and the top-left corner of the Infusion Kit.

The figure describes the various steps of preparing and administering a bolus according to the present invention.

Figure 1:
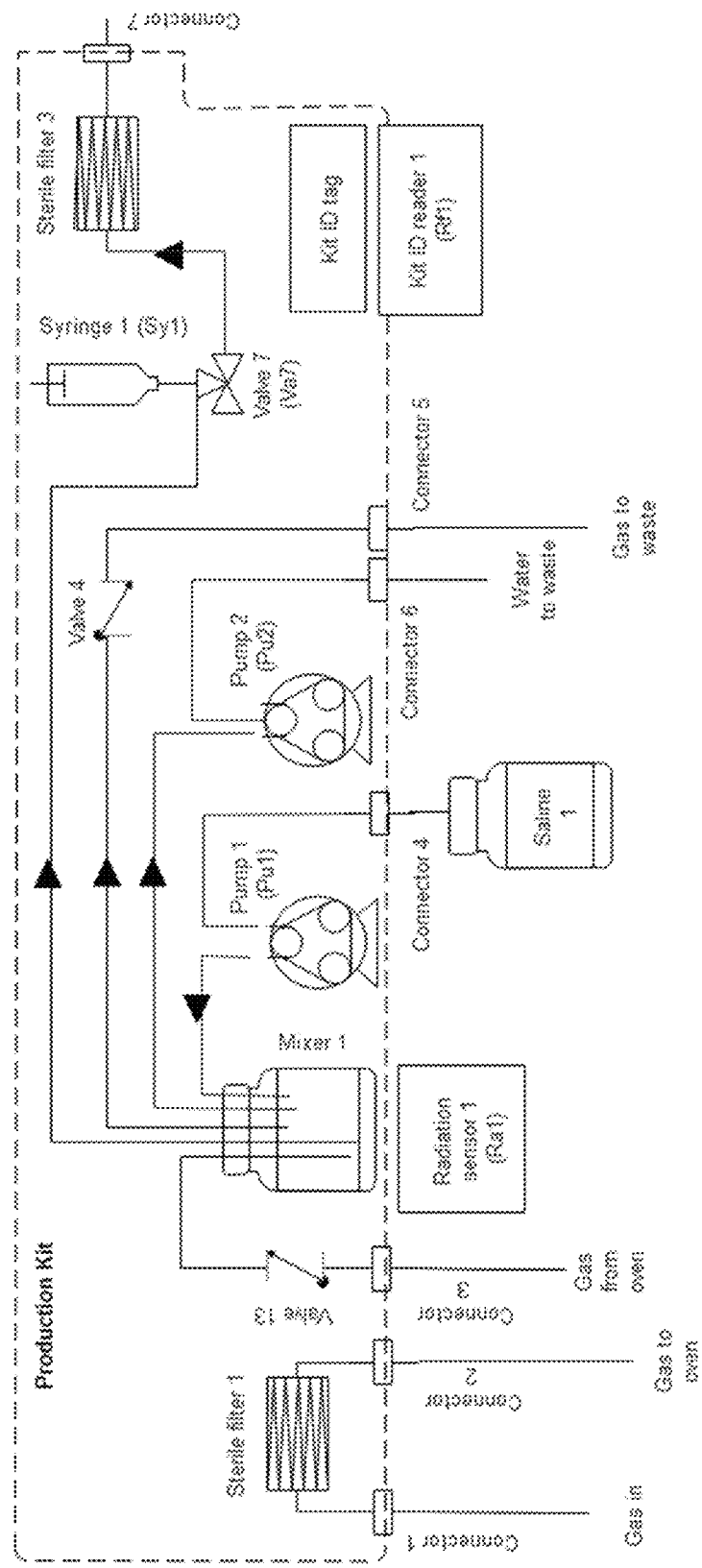
FIG. 1 and FIG. 2 are schematic flow charts for the system according to the present invention. The system comprises two parts: The Production Kit and the Infusion Kit, which for convenience are shown as two separate figures.
Figure 2:
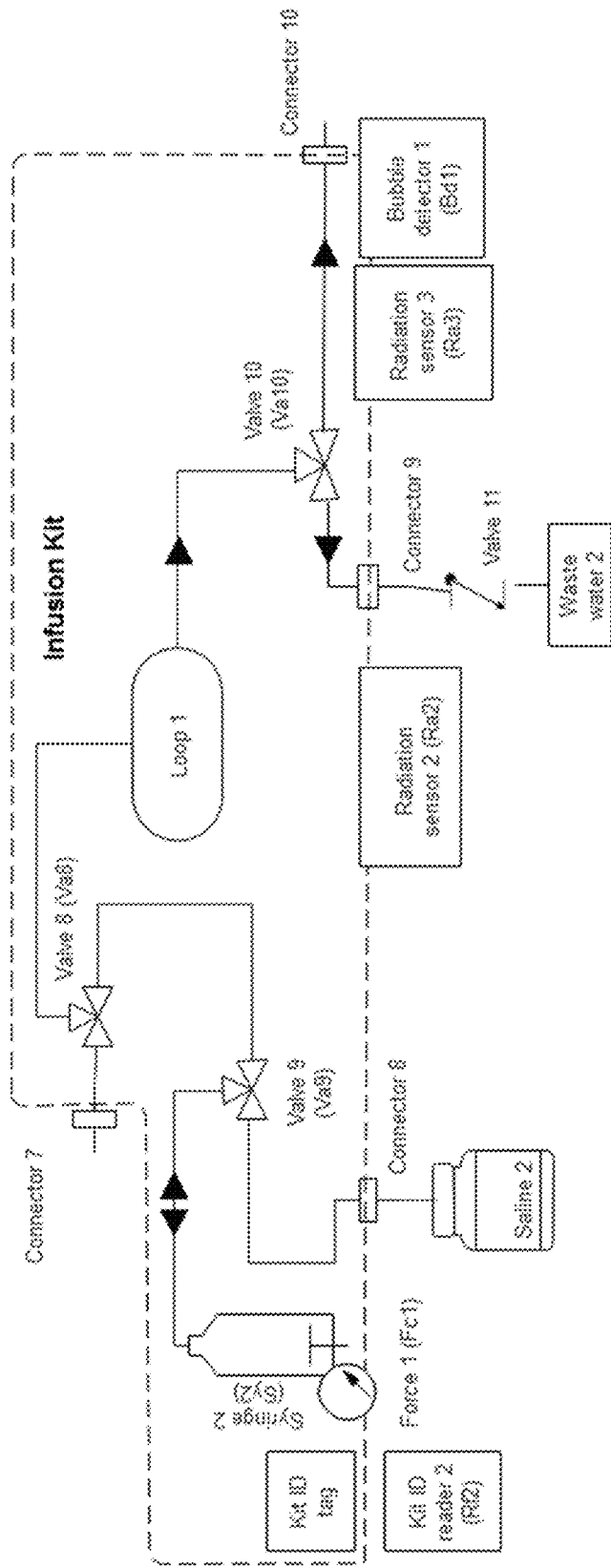

Step 1: The illustration represents a static situation in which the injection system has been primed with saline from the saline reservoir all through the tube length between L1 and L2 and further until the awaiting patient. L1 and L2 correspond to Valve 8 and Valve 10 depicted in FIG. 2, respectively. A second reservoir containing a radioactive tracer intended for dosing and injection into the patient is connected to the injection system.

Step2: The illustration represents a dynamic process, in which the radioactive tracer in the connected reservoir is pumped or pushed into the injection system. Suitable means for pumping or pushing can be any known to man, but preferably the radioactive tracer is pumped or pushed by a compressible gas which could be sterile air at low pressure. In doing so the radioactive tracer solution fills the ventilated sterile filter, and displaces the saline present between L1 and L2 towards waste. At the interface between the incoming radioactive tracer solution and the displaced saline, some mixing of the two aqueous solutions will take place.

Step3: The illustration represents a dynamic process, as a continuation of step 2. The radioactive tracer has now filled the entire tube length/reservoir between L1 and L2, and the interface between the radioactive tracer and saline solutions has been pushed into the waste line connection. As a result, the space between L1 and L2 now contains a homogenous bolus of radioactive tracer having an indistinguishable radioactivity concentration difference between any two points within the volume and/or boundaries of the bolus.

Step 4: The illustration represents a static situation in which the dynamic steps of 2) and 3) have come to an end. When the means to pump/push the radioactive tracer forward includes the preferred embodiment of compressed gas, the ventilated filter will expel the overpressure, and the radioactive tracer solution now partly fills the ventilated sterile filter as well as the full length of the space between L1 and L2, and in part the waste line. The interface between the radioactive tracer and saline solution is pushed far into the waste line.

Figure 5:
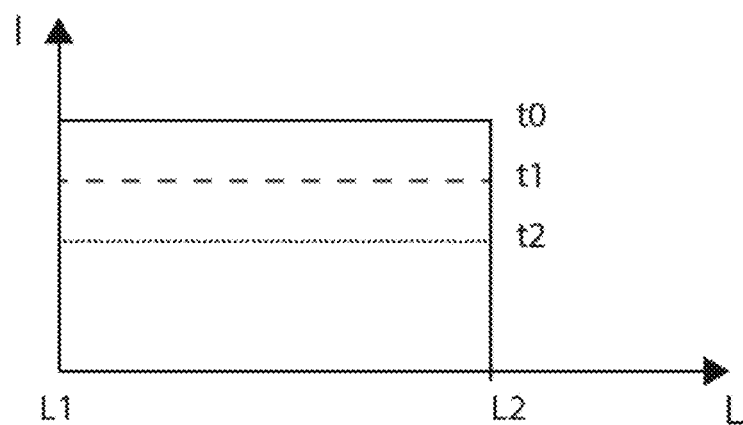
Figure 5:
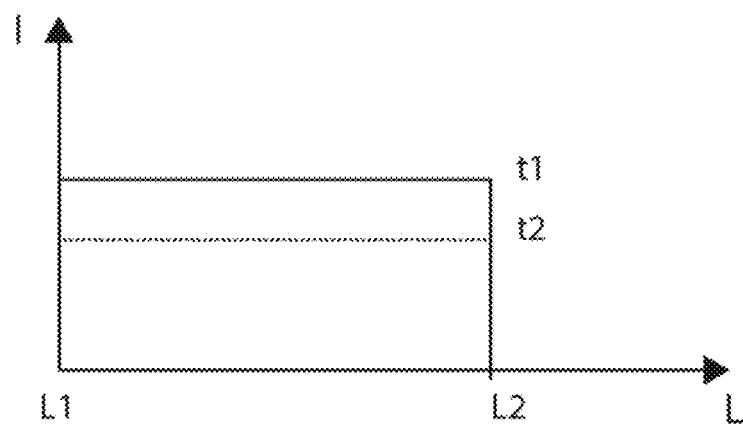
Figure 5:
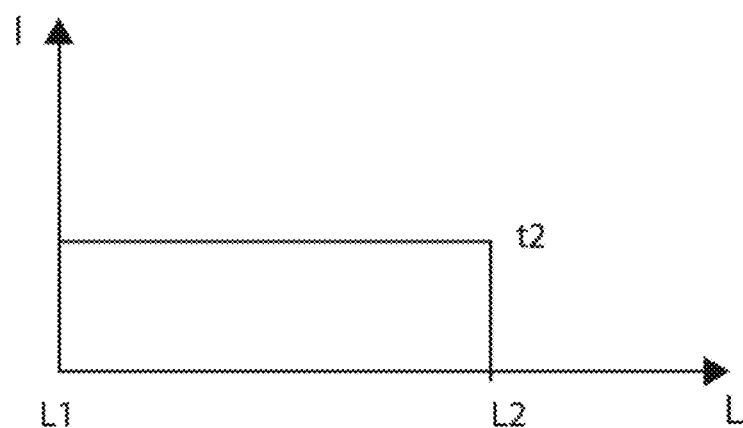

Step 5: The illustration represents a static situation following 3) and 4), in which the radioactivity sensor measures the radioactivity of solely the tube length L1-L2. L1 and L2 represent valves 8 and 10, respectively (see FIG. 2), which at Step 5 have been oriented into a position to close off the radioactive tracer bolus between L1 and L2 from any physical contact with other liquids. The radioactivity concentration will be homogenous across the entire tube length/reservoir L, as indicated in FIG. 5. Given that the tube length and inner diameter are known, the radioactivity concentration of the radioactive tracer bolus intended for injection expressed as activity/unit volume can be determined with great precision. Furthermore, as time progresses, radioactive decay will reduce the radioactive concentration proportional to the halflife of the radioactive tracer. However, regardless of the radioactive decay, the radioactivity concentration along the tube length/reservoir, defined by the space between L1 and L2, will remain homogenous.

Step 6: The illustration represents a dynamic situation following step 5. Upon reaching the desired radioactivity concentration expressed as activity/unit of volume, the saline reservoir through means of pumping/pushing initiates the injection of the radioactive tracer bolus into the patient. The initiation of injection will cause the primed saline between L2 and the patient to be injected in a manner proportional to the saline entering at L1, while propelling the radioactive tracer bolus across the tube length L1-L2 and further towards the patient.

Step 7: The illustration represents a dynamic situation as a continuation of step 6. In this situation, the entire radioactive tracer bolus has been propelled across the tube length/reservoir L1-L2 and is on its way to the patient. The radioactivity sensor (not depicted) will no longer sense any radioactivity.

Step 8: The illustration represents a dynamic situation as a continuation of steps 6) and 7). In this situation, the entire radioactive tracer bolus has left the tube length L1-L2 and continues across the connected tube into the awaiting recipient or patient.

FIG. 4

Figure 3:
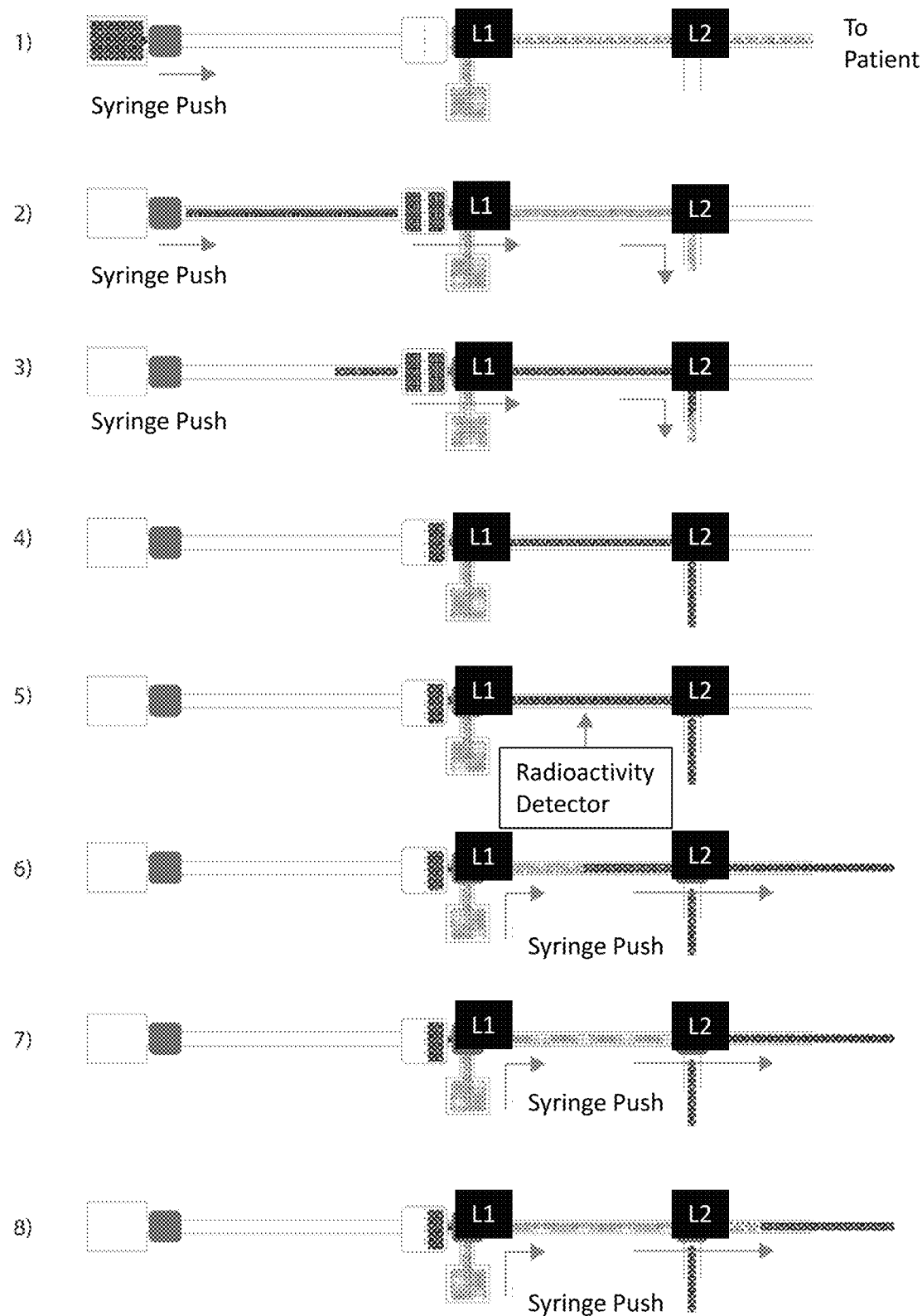
FIG. 3
Figure 4:
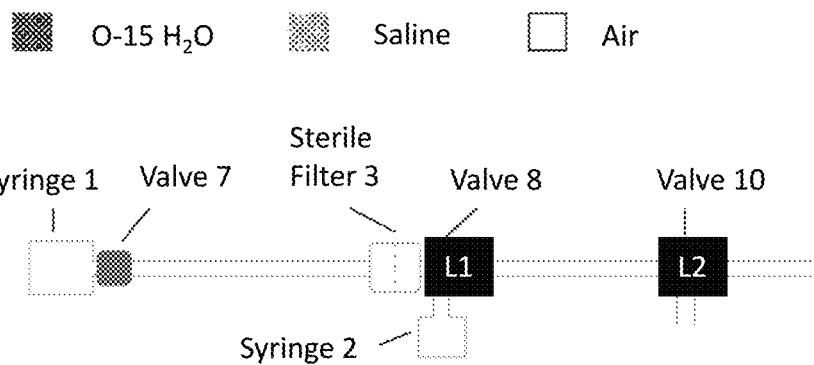

FIG. 4 shows the legend for FIG. 3.

FIG. 5

The collection of figures describes in theoretical terms the bolus homogeneity in activity (I) across the tube length (L), as a result from the proposed invention.

First graph: The illustration is a static description of the activity concentration pr. unit of tube length between L1 and L2, following the previous step 5). The activity will be homogenous across the tube length, and is represented as the solid line corresponding to t0. When inferring the radioactive tracer's halflife, the activity level at further time points t1 and t2 can be extrapolated, and since L1 and L2 are valves (valve 8 and 10, respectively—please see FIG. 2) and oriented in a manner not allowing for contact between the radioactive tracer bolus and other media, no osmotic or diffusion effects will influence the bolus homogeneity over time.

Second Graph: The illustration is a static description following a time span from t0 until t1. The activity will be homogenous across the tube length, and is represented as the solid line corresponding to t1. When inferring the radioactive tracers halflife, the activity level at further time points t2 can be extrapolated.

Third Graph: The illustration is a static description following a time span from t0 until t2. The activity will be homogenous across the tube length, and is represented as the solid line corresponding to t2.

FIG. 6

The collection of figures describes the conventional methodology whereby a radioactive tracer can be preloaded into an injection system, by which means the radioactivity concentration as described by activity/unit volume will be influenced by osmotic, diffusion and mixing effects. While the total radioactivity might be known, the absolute radioactivity concentration at any given point will become increasingly uncertain as time elapses due to osmotic, diffusion and mixing effects.

Panel 1: The illustration is a static description of a saline reservoir connected to a tube, which is further connected to a recipient or a patient. The tube length is sufficiently long to allow for a volume larger than the volume of the intended dose of radioactive tracer solution. The entire tube length has previously been primed with saline. The radioactive tracer solution is housed in a reservoir which is further connected to the injection system.

Panel 2: The illustration is a dynamic description following Panel 1. By means of pumping/pushing, the dose of radioactive tracer solution is transferred into the tube length. At the interface between the incoming radioactive tracer solution and the saline present in the tubing, mixing of the two aqueous solutions will take place immediately.

Panel 3: The illustration is a dynamic description following Panel 2. The dose of radioactive tracer solution enters further into the length of tubing primed with saline, and the mixing effect at the solvent interface becomes more pronounced.

Panel t0: The illustration is a static description following Panel 3. The entire dose of radioactive tracer solution has now been loaded into the length of tubing, and the mixing effects at the solvent interface are at their maximum.

Panel t1: The illustration is a static description following Panel t0, in which a time span t0-t1 has elapsed. During this time span, osmotic and diffusion effects come into play, herewith offsetting the radioactive tracer concentration along the tube length further.

Panel t2: The illustration is a static description following Panel t1, in which a time span t0-t2 has elapsed. The longer the time span, the more pronounced the osmotic and diffusion effects will become, leading to the homogeneity of the radioactive tracer concentration along the tube length being even further offset.

FIG. 7

The collection of figures describes in theoretical terms the lack of bolus homogeneity of radiopharmaceuticals as a result of current methodology for preloading the radioactive tracer/bolus into an injection line/system primed with saline.

First graph: The illustration is a static description of the activity concentration pr. unit of tube length between L1 and L2. The denotation of L1 and L2 are meant for comparison with the previous FIG. 3. Following the previous step, the activity will not be homogenous across the tube length, but will have a shape represented by the solid line in the graph for to. The reason for the non-homogeneity is ascribed to the initial mixing between the radioactivity tracer solution and the saline already present in the tubing during loading of the radioactivity tracer into the tube length. Even further, as time progresses, osmotic and diffusion effects will spread out the activity over an increasing length of tube, and thus even if the activity in total in the tube length is known, the volume cannot be known. The total distributed volume of the radioactive tracer has increased.

Second Graph: The illustration is a static description following a time span from t0 until t1. The activity will not be homogenous across the tube length, and is represented by the solid line corresponding to t1. Notably the total distributed volume of the tracer has further increased from time=t0 to t1.

Third Graph: The illustration is a static description following a time span from t0 until t2. The activity will not be homogenous across the tube length, and is represented as the solid line corresponding to t1. Notably the total distributed volume of the tracer has further increased during the time span t1 to t2.

Figure 8:
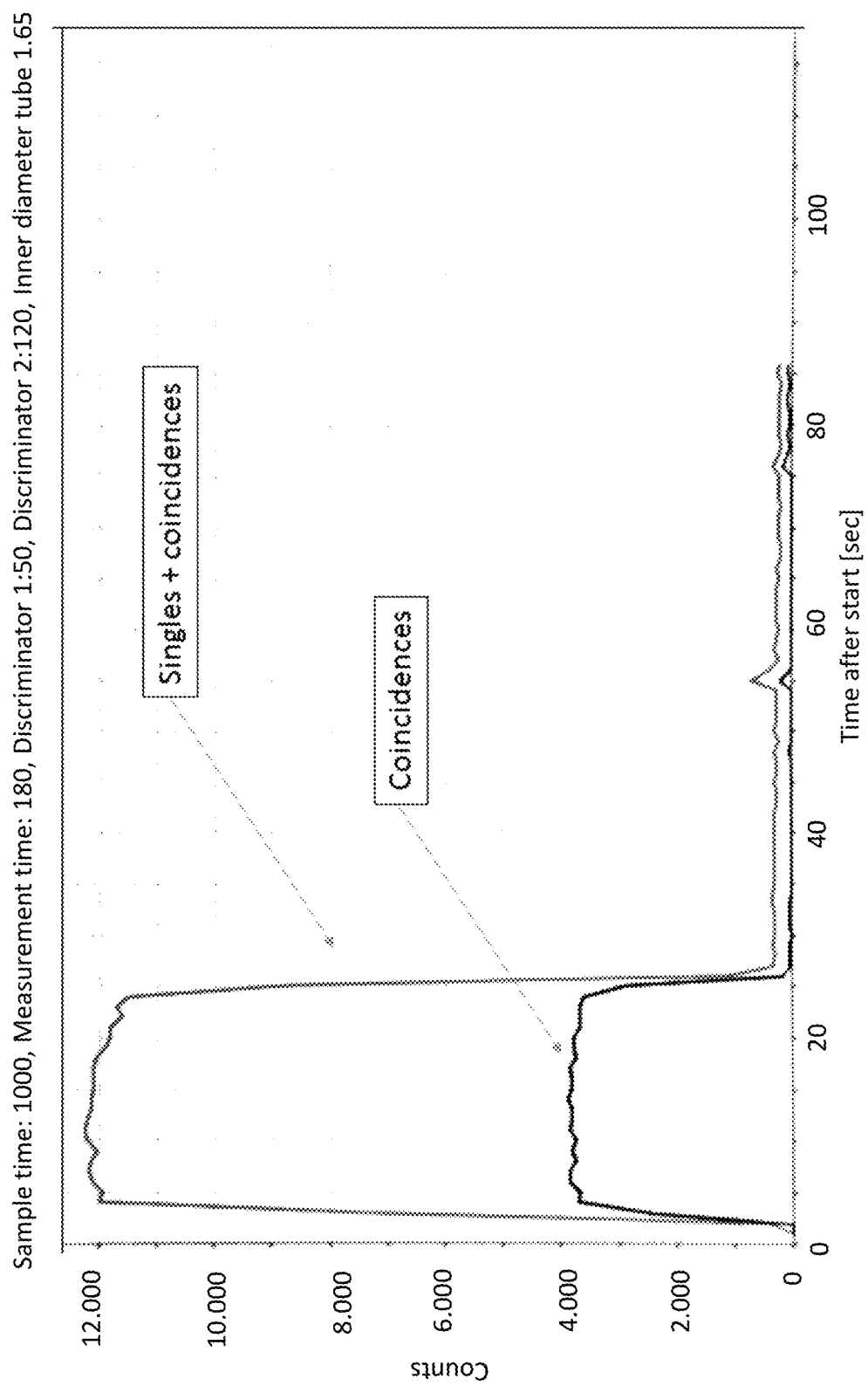
Figure 9:
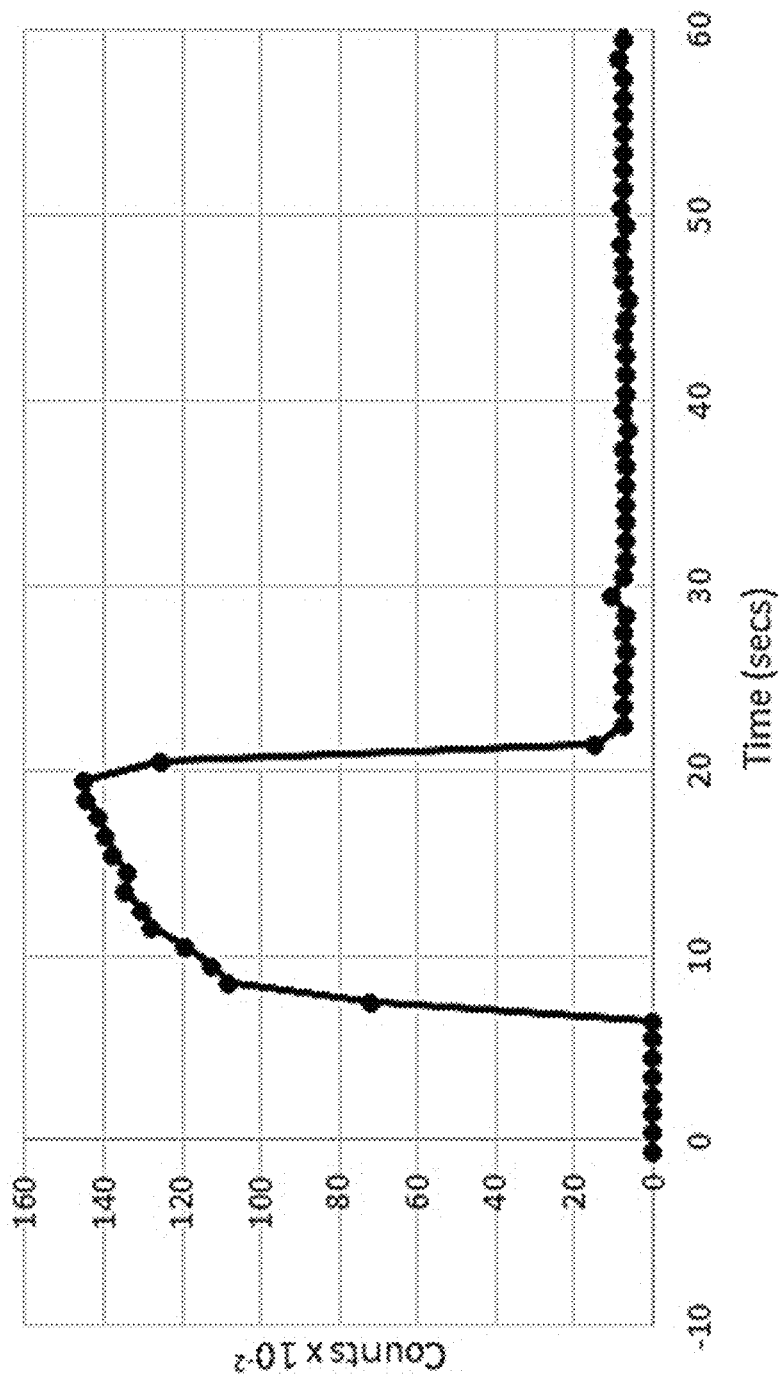
Figure 10:
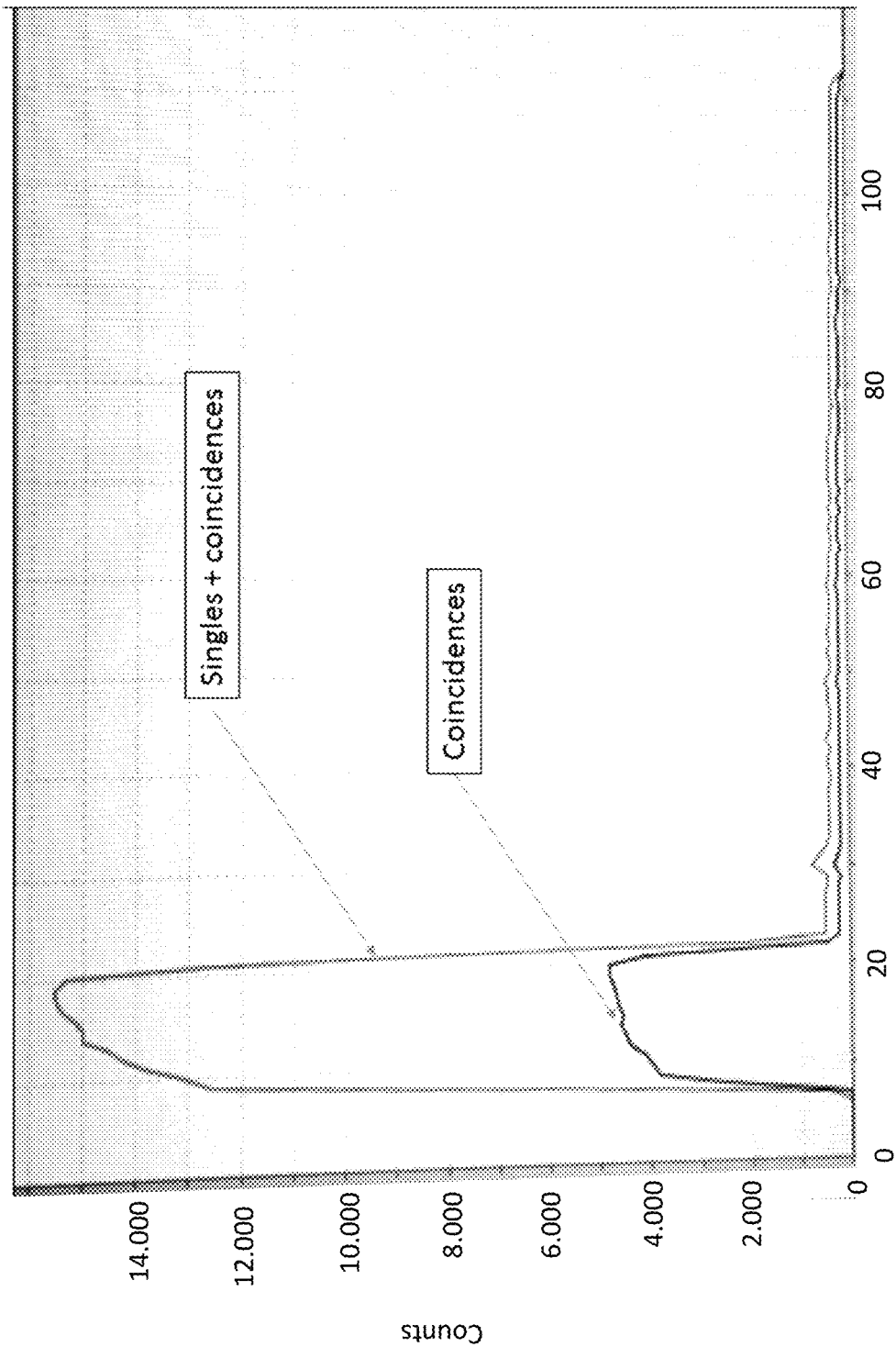
Figure 11:
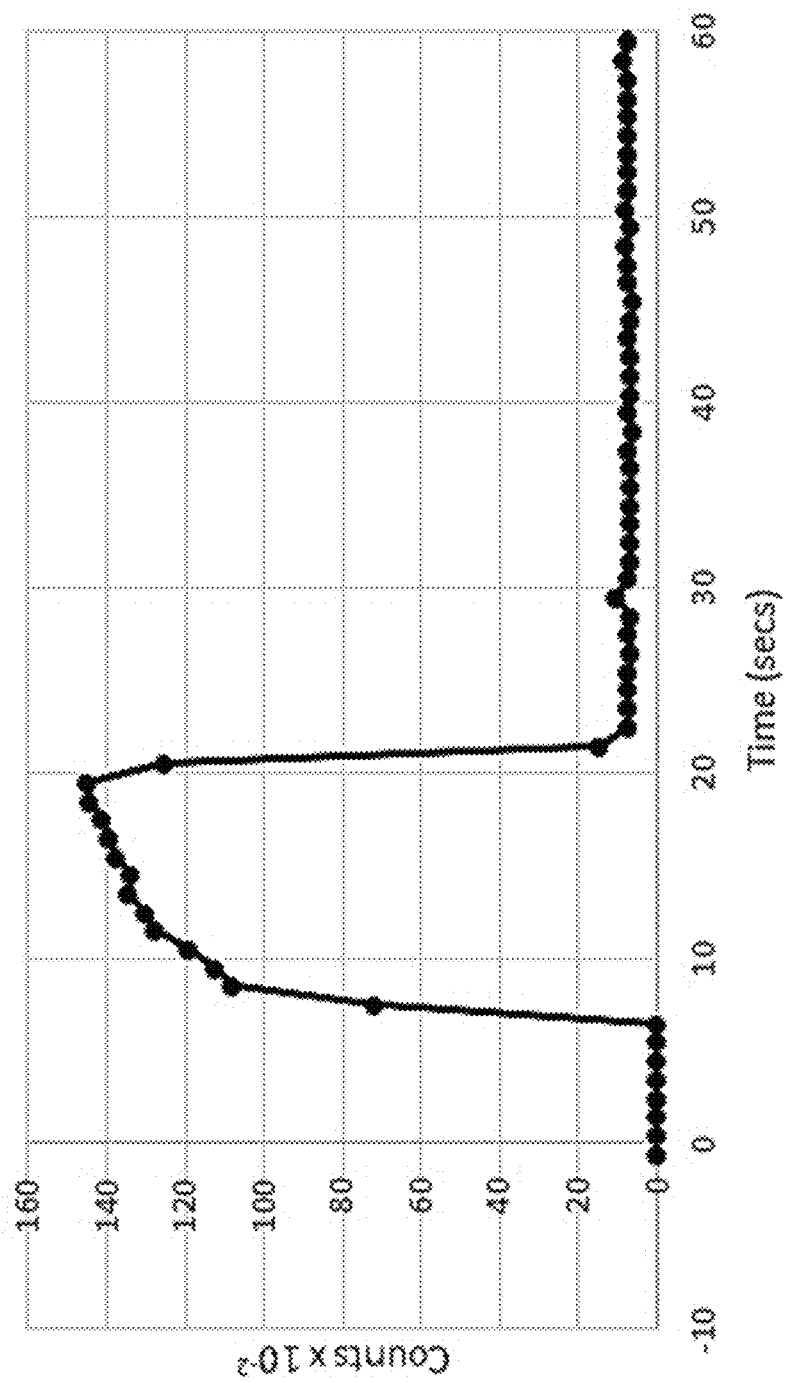

FIGS. 8-11 show the results of experimental measurements of the radioactivity profile of a bolus delivered according to the present invention (FIGS. 8 and 9) and according to conventional methodology (FIGS. 10 and 11). FIGS. 8 and 10 show photos of the monitor displaying the radioactivity measurements as a function of time, and FIGS. 9 and 11 show graphs representing the data from the measurements. For experimental setup, see the Examples section.

DETAILED DESCRIPTION OF THE INVENTION

The administered dose (D) dose of a radiopharmaceutical having a radioactive halflife of <21 minutes should be of a size suitable to the detection limit of the scanner, local scanner settings and conditions as well as the individual patients age, weight, sex and ethnicity. It is foreseen that the size of (D) shall likely decrease from current levels with the advent of improved detection capabilities of PET-scanners, and also drop by changes in legislation to fulfill the "As Low As Reasonably Achievable" (ALARA) principle, but (D) shall never decrease to or beyond a point by which the principal fulfilment of the diagnostic reasons for administering the dose become impossible. (D) is likely to be within the range of 5 MBq up to 5.000 MBq, but currently (D) will be preferably within the 250-500 MBq range, and in the near future preferably within the 100-250 MBq range. In the distant future (D) will be preferably be within 10-100 MBq. Most preferably (D) is 400 MBq plus or minus a range of up to 10% permissible as std. variations of radioactive activity dose administrations within the practice of medicine.

The bolus volume (V) should be of a size to allow for a rapid introduction into the body, and suitable as regards the individual patients age, weight, sex and ethnicity. For different diagnostic purposes (V) will be within the range of 0.05-50 ml. Preferably (V) will be within the range of 1-5 ml, and most preferably (V) is 2 ml plus or minus a range of up to 10% permissible as std. variations for pharmaceutical volume administrations within the practice of medicine. It is foreseen that the size of (V) may decrease from current levels with the advent of improved administration lines or pump functionalities. The injection speed (S) should be sufficiently fast to allow for rapid introduction of the volume (V) into the body, and suitable as regards the individual patients age, weight, sex and ethnicity. (S) will be within the range of 0.1 ml/s-5 ml/s, and preferably within the range of 1 ml/s-3 ml/s. (S) is most preferably 2 ml/s. It is likely that (S) may increase with the advent of improved PET scanner data acquisition from radiation detectors. However, lower injection speeds may also become relevant for certain applications of the present invention.

In a first aspect the invention relates to a bolus for non-surgical, intravenous (IV) administration to a recipient comprising a liquid solution of a radiopharmaceutical having a radioactive half-life of <21 minutes for use in blood flow imaging, characterized in that said bolus has a substantially cylindrical body and an unvarying (homogeneous) radioactivity profile throughout the volume of the bolus.

In an embodiment of the first aspect said bolus has a substantially cylindrical body and an homogeneous radioactivity distribution throughout the volume of the bolus. In another embodiment of the first aspect said bolus has a substantially cylindrical body and a homogeneously distributed radioactivity content throughout the volume of the bolus.

In another embodiment said bolus has a substantially cylindrical body and a constant radioactivity profile measured along the longitudinal axis of said substantially cylindrical body.

In an embodiment of the first aspect said bolus has a substantially cylindrical body and an indistinguishable radioactivity concentration at any point within the volume and/or boundaries of the bolus.

In an embodiment said bolus has a substantially cylindrical body and a negligible difference in radioactivity concentration between any two points within the volume and/or boundaries of the bolus.

In an embodiment the isotopes of the radiopharmaceutical are selected from isotopes capable of undergoing beta plus decay (positron emission) such as: C-11 (radioactive half-life app. 20.4 min), N-13 (half-life app. 9.97 min), Cu-62 (half-life app. 9.74 min), K-38 (half-life app. 7.64 min), I-122 (half-life app. 3.6 min), O-15 (half-life app. 122 sec), Rb-82 (halflife app. 75 sec) or O-14 (half-life app. 70.6 sec).

In another embodiment, the isotopes of the radiopharmaceutical are selected from a group comprising isotopes capable of undergoing beta minus decay such as: O-19 (half-life app. 26.5 sec) and O-20 (half-life app. 13.5 sec).

In yet another embodiment the isotopes of the radiopharmaceutical are selected from a group comprising isotopes capable of undergoing alpha decay.

In yet another embodiment the isotopes of the radiopharmaceutical are selected from a group comprising isotopes capable of Auger electron emission.

In an embodiment the radiopharmaceutical has a radioactive half-life less than 21 minutes. In a preferred embodiment the radiopharmaceutical has a radioactive half-life less than 10 minutes. In a most preferred embodiment the radiopharmaceutical has a radioactive half-life less than 3 min.

A particularly interesting radiopharmaceutical in relation to the present invention is radioactive water, such as O-15 H2O. Radioactive water is inert in the sense that it is not bound to any tissue or specific organs, but is distributed freely in the organism.

In a preferred embodiment the radiopharmaceutical is thus radioactive water, such as O-15 H2O or 014-H2O.

In another preferred embodiment the blood flow imaging is performed using PET (positron emission tomography) or SPECT (photon emission computed tomography) scanning methodology.

In a second aspect the invention relates to a bolus as defined in the first aspect of the invention for use in the non-surgical diagnosis of a disease or medical condition selected from tumor hypoxia, apoplexy including ischemic apoplexy, vascular dementia, renal failure, muscular ischemia, myocardial ischemia, general microvascular disease, vasculitis, pancreatic failure and other conditions related to blood flow impairment, or for use in the modelling of a human heart, and/or chambers and cavities therein, such as the left and right atrium as disclosed in co-pending international patent application PCT/DK2017/050367.

In an embodiment the disease or medical condition is inferred from failure in or reduction of the tissue microvasculature or the body microvasculature. In another embodiment the disease or medical condition is cerebral apoplexy. In another embodiment the disease or medical condition is renal failure resulting from reduced blood flow.

In a preferred embodiment the disease or medical condition is tumor hypoxia. In another preferred embodiment the disease or medical condition is myocardial ischemia.

In a third aspect the invention relates to a non-surgical method for preparing and administering a bolus according to the first or second aspect of the present invention, which method comprises:

Providing a source of a liquid solution of a radiopharmaceutical having a radioactive half-life of less than 21 minutes, providing a first valve having a waste position and a recipient position, providing a bolus conduit (a), a waste conduit (b) and a recipient conduit (c), each conduit having a valve end being connected to said first valve, so that the first valve can establish a waste flow path in the waste position and a recipient flow path in the recipient position, the recipient flow path being different from said waste flow path, the bolus conduit comprising a measuring section and an internal volume, the internal volume being approximately equal to the selected volume of the radioactive solution to be delivered to the recipient, arranging said first valve in the waste position, transporting a first amount of said radioactive solution through said waste flow path, the first amount of said radioactive solution having an initial level of radioactivity that is at least approximately equal to or higher than the selected level of radioactivity and a volume that is larger than the internal volume of said bolus conduit, providing a radiation detector, the radiation detector being operable to measure a level of radioactivity of the radioactive solution in said measuring section, measuring a reference level of radioactivity of said radioactive solution present in said measuring section, characterized in that when the reference level of radioactivity is approximately equal to a predetermined injection level of radioactivity, the method further comprises the steps of:

arranging the first valve in the recipient position, and transporting the radioactive solution present in the bolus conduit through the recipient flow path.

In an embodiment of the third aspect the source conduit (a) comprises a source inlet adapted to receive the radiopharmaceutical solution from the source, the waste conduit comprises a waste outlet adapted for flow of said solution out of said waste conduit (b) and the recipient conduit (c) comprises a recipient outlet adapted for flow of said solution out of said recipient conduit to a recipient.

In prior art systems for the handling of radiopharmaceuticals some of the employed isotopes have a relatively long half-life, such as F-18 (half-life: 109.8 minutes) which is used in the production of F-18 labeled fluorodeoxyglucose (FDG), compared to O-15 water which is based on O-15 having a half-life of 122 seconds. The production time for these radiopharmaceuticals is typically also considerably longer (about 4 hours for F-18 FDG vs. about 5 min for 0-15 water). This means that both the production costs and longer half-life of F-18 FDG makes it a valuable asset for a period of time, as only half the original activity is gone after about two hours. 10% of the original activity is still left after about 6 hours. F-18 FDG therefore has an actual shelf life, albeit a short one, and it makes sense to plan for using excess produced FDG within a normal working day. This is not the case with O-15 water, because its short half-life renders it practically worthless very quickly. Only 10% of the original activity in freshly produced O-15 water is left after about 6 minutes and less than 1% after 15 minutes.

Furthermore, to obtain a liquid solution of a radiopharmaceutical which can be transported to the recipient, prior art systems have to apply a partially manual mixing and dilution of the highly radioactive isotopes (such as eg. F-18 labeled FDG) with a dilution liquid such as saline in a plurality of different containers. These issues make the prior art systems relatively complex. Another problem is the inaccurate determination of the radioactivity of the dose of radioisotopes at a given time-point.

The infusion system and method of delivering a liquid solution of a radiopharmaceutical according to the present invention overcome these issues in a much simpler way by overfilling a loop having a precisely defined volume with the liquid solution of a radiopharmaceutical until the point where the contents of the loop have reached a desired, steady state activity level at which point the filling procedure is interrupted and the contents of the loop left to rest until another predetermined activity level is reached by radioactive decay, at which point the contents of the loop are injected into the recipient, thus avoiding the need to add more diluting liquid or radioactive isotopes after the loop has been filled. This method is presented graphically in FIG. 3 and FIG. 5. FIG. 5 illustrates the unvarying (homogeneous) radioactivity profile throughout the volume of the bolus.

By this method a very precisely defined amount of radioactivity can be delivered in a bolus having a very precisely defined volume and an unvarying (homogeneous) radioactivity profile throughout the volume of the bolus. Moreover, due to the very short production time in the system according to the present invention, the necessary volume for containing a predefined dose of radioactivity is relatively small when compared to systems which use a high number of half-lifes in order to produce a dose ready for administration. For radiopharmaceuticals having a half-life of less than 21 minutes, the prior art radioactive boluses/ doses thus typically become more highly diluted than obtainable by the system according to the present invention. This problem is presented graphically in FIG. 6 and FIG. 7. FIG. 7 illustrates how the radioactivity profile varies along the longitudinal axis of the injected dose.

The system of the present invention thus primarily differs from the prior art by enabling the administration of a highly accurate dose of radioactivity in a well-defined bolus, and due to the very short overall production time further enables the delivery of said short-lived radiopharmaceutical in a relatively small volume, such that the final bolus may have a relatively high radioactivity concentration.

In another embodiment of the third aspect the first amount of said radioactive solution has a volume that is 1-2 times larger than the internal volume of the bolus conduit.

In an embodiment of the first, second or third aspect the bolus of the radiopharmaceutical contains a radioactive dose of 250-1000 MBq, such as 400 MBq-1000 MBq, 250-500 MBq, preferably 360-440 MBq, such as 400 MBq. In another embodiment the bolus of the radiopharmaceutical contains a radioactive dose of 100-250 MBq. In yet another embodiment the bolus of the radiopharmaceutical contains a radioactive dose of 10-100 MBq.

In an embodiment of the first, second or third aspect, said bolus has a high radioactivity concentration, such as between 50-500 MBq/ml, preferably 180-220 MBq/ml, such as 200 MBq/ml.

It is to be understood that the bolus conduit (depicted as "Loop 1" between valve 8 and valve 10 in FIG. 2) is overfilled with the homogeneous radioactive solution so that the relevant radiopharmaceutical still has a sufficiently high level of radioactivity left for use in blood flow imaging, when the bolus conduit is completely filled. This is also applicable for isotopes with half-lifes less than 3 minutes.

In another embodiment of the third aspect, the liquid solution of a radiopharmaceutical is delivered to the recipient with an injection speed (S) of approximately 0.05-7 ml/sec, preferably approximately 1-5 ml/sec, such as 2 ml/sec and most preferably approximately 1 ml/sec. The preferred volume V of the delivered bolus is 2 ml.

In another embodiment of the third aspect, the liquid solution of a radiopharmaceutical is held in the bolus conduit for a relevant holding time until a desired radioactivity level is attained by natural radioactive decay, before being delivered to the recipient.

In another embodiment of the third aspect, the duration of the administered bolus is from 0.3-5 sec, preferably 1 sec, said bolus containing a delivered radioactivity (D) of 5 MBq up to 5.000 MBq, preferably (D) is within the 250-1000 MBq range, such as 400 MBq-1000 MBq or 250-500 MBq range. Most preferably (D) is 400 MBq plus or minus a range of up to 10% permissible as std. variations of radioactive activity dose administrations within the practice of medicine.

The advantages of using the herein described dose of a radiopharmaceutical having a radioactive half-life of less than 21 minutes, such as O-15 H2O in the form of a known radioactive dose (D), a known volume (V) and a known injection speed (S) in conjunction with a PET-scanner in order to qualitatively or quantitatively measure the tumor blood flow and related parameters, are that the radiation exposure to the patient is reduced due to the short half-life of such radiopharmaceuticals, when compared to other radioactive tracer modalities, thus fulfilling the ALARA principle. In addition, the homogenous and reproducible characteristics of using the described dose with respect to age, weight, sex and ethnicity allows for the creation of large normal and abnormal databases from which new treatment strategies and dosing strategies can be developed for treating the individual, relevant disease or medical condition in a personalized manner.

Furthermore the quantitative possibilities within PET-scanning technologies for flow and perfusion within oncology and other medical areas rests on the capability to create reproducibly the dose as herein described, but given the dose be administered as described, the PET-scanning technology combined with software algorithms will allow for the quantification of flow and perfusion within an in vivo region of interest, which may further be coupled to the treatment and dosing strategy in a relative and qualitative manner so that the individual patient's medication or radiation treatment plan can be either up or down regulated depending on the established flow and/or perfusion through the tumor or other tissue.

Finally, the repeated administration of a radiopharmaceutical having a radioactive half-life of less than 21 minutes, such as O-15 H2O in a manner as described herein, but over the course of days, weeks or months can serve as a treatment response tool for evaluating the efficacy of treatment by a chosen treatment modality, i.e. radiation treatment or administered drugs, but also in treatment strategies where e.g. the treatment of the oncologic disease state of the patient rests upon firstly reducing the hypoxic areas or elements of the tumor or by opening the capillaries within the tumor in order to improve the relative dose uptake to the tumor of IV administered drugs.

In a fourth aspect the invention relates to a bolus as defined in the first aspect of the invention for use in radionuclide therapy, wherein the radiopharmaceutical having a radioactive half-life of less than 21 minutes is based on a beta- or alpha-emitting radioisotope, or an Auger electron emitting radioisotope.

Targeted radionuclide therapy is one of the most intensively developing directions of nuclear medicine. Unlike conventional external beam therapy, the targeted radionuclide therapy causes less collateral damage to normal tissues and allows targeted drug delivery to a clinically diagnosed neoplastic malformation, as well as metastasized cells and cellular clusters, thus providing systemic therapy of cancer. The methods of targeted radionuclide therapy are based on the use of molecular carriers of radionuclides with high affinity to antigens on the surface of tumor cells. The potential of targeted radionuclide therapy has markedly grown nowadays due to the expanded knowledge base in cancer biology, bioengineering, and radiochemistry. The targeted radionuclide therapy is based on the use of high-affinity molecules as carriers of radionuclides to tumor cells. Pharmaceuticals for targeted radionuclide therapy are often injected intravenously or intracavitary. Following the injection, such drugs enter the blood stream and eventually reach their target—a target molecule on the surface of tumor cells. A radionuclide attached to the pharmaceutical directly interacts with the rumor cell.

In an embodiment of the fourth aspect of the present invention the employed radiopharmaceutical is a molecular carrier of a radionuclide having a radioactive half-life of less than 21 minutes with high affinity to a relevant antigen on the surface of tumor cells, such as PIB radiolabelled with C-11, or a peptide component radiolabeleld with N-13, C-11 or similar radioisotopes capable of undergoing beta plus decay. In a further embodiment the molecular carrier could be identical with the radioisotope capable of undergoing beta minus decay, alpha decay or auger electron emission.

Examples

The radioactivity homogeneity of a bolus according to the present invention was measured in the following way:

A. Measurements of a Bolus According to the Present Invention (See FIGS. 3, 5, 8 and 9)

A loop of 3 ml volume (Coiled Low pressure Connector Tubing, Bayer, Lot nr. 8404710, internal diameter 1.65 mm) initially filled with saline, was continuously filled with radioactive water (15-O water) through L1 and the overflow led to waste through L2, corresponding to FIGS. 3.1-3.3. L1 and L2 correspond to Valve 8 and Valve 10 in FIG. 2, respectively.

When the experiment started, the flow through L1 and L2 was stopped, and the two valves closed to establish a well-defined bolus of 3 ml, corresponding to FIGS. 3.4 and 3.5. The radioactivty profile of the bolus was next established by pumping the bolus past a detector (Allogg A B, Mariefred, Sweden) with a constant flow rate of 7 ml/minute. Radioactivity concentrations were measured every 1.0 sec, and corrected for radioactive decay to the start of tracer administration.

The radioactivity concentration measurements are shown in FIG. 8 (monitor photo) and FIG. 9 (Excel graph) as a function of time, and show that the radioactivity concentration is practically identical for the whole duration of the experiment, ie for the whole length of the bolus.

When the bolus according to experiment A is ready for injection—either at once or after a relevant holding time in order to arrive at certain radioactivity level—the radioactivity concentration will remain constant throughout the volume of the bolus, also when radioactive decay diminishes the total radioactivity of the bolus, allowing for precise determination of the bolus volume as well as activity for any given time point. This corresponds to the theoretical decay graphs shown in FIG. 5.

For comparison reasons a conventionally delivered dose of radioactive water was measured for homogeneity when delivered into a volume of saline water.

B. Measurements According to Conventional Technology (See FIGS. 6-7 and 10-11)

Figure 6:
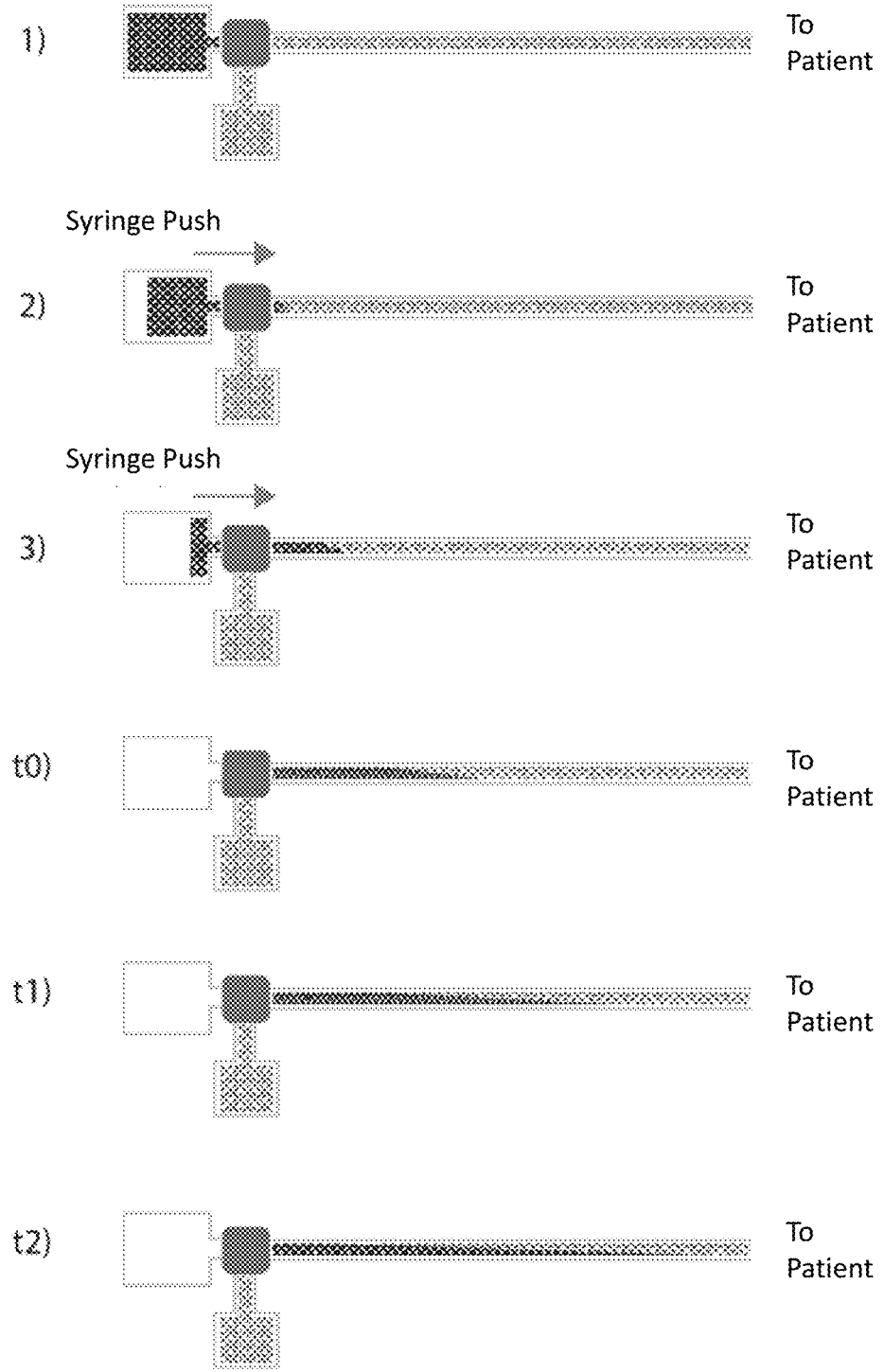
Figure 7:
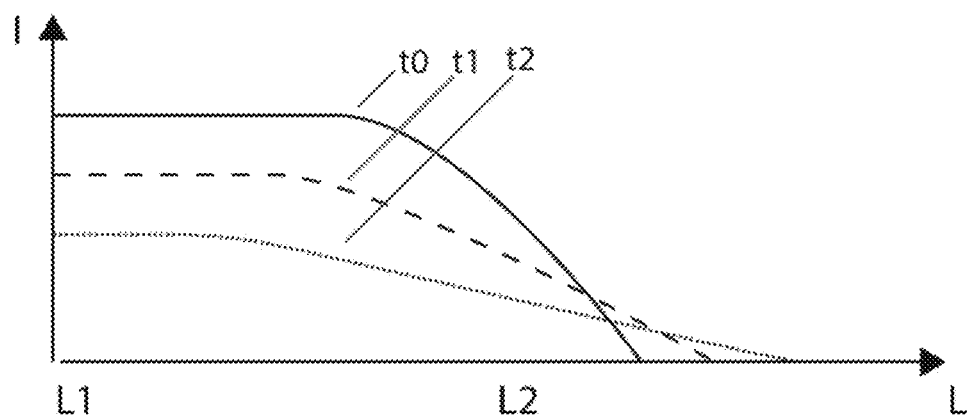
Figure 7:
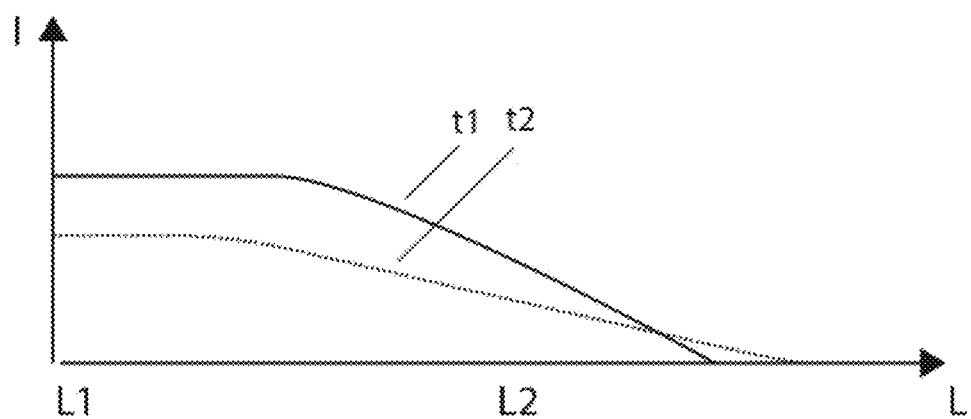
Figure 7:
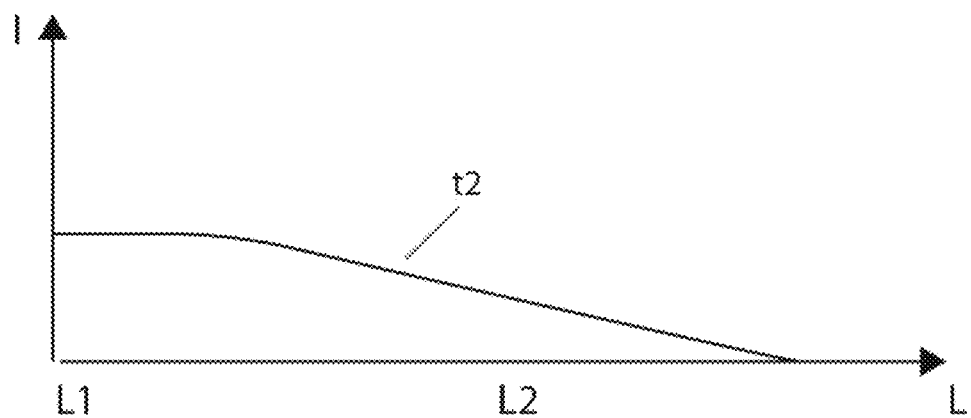

Into a loop of tubing (same type as for experiment A), initially filled with saline, was injected a volume of radioactive water (15-O water), roughly corresponding to half the volume of the length of tubing, similar to the situation depicted in FIGS. 6.1-6.3.

The radioactivty profile of the injected dose of radioactive water was next established by pumping the contents of the length of tubing past a detector (Allogg A B, Mariefred, Sweden) with a constant flow rate of 7 ml/minute. Radioactivity concentrations were measured every 1.0 sec, and corrected for radioactive decay to the start of tracer administration.

The radioactivity concentration measurements are shown in FIG. 10 (monitor photo) and FIG. 11 (Excel graph) as a function of time, and shows that the radioactivity concentration is sloping rather than constant. As the front of the injected dose of radioactive water is closer to the Allogg detector, the initial measurements (lower time values) show a lower concentration than the later measurements (higher time values), indicating that the front of the injected dose has become mixed with saline, whereby the concentration is lowered. The total activity of the injected dose is not affected by the mixing, but the volume containing the radioactive dose is no longer precisely known.

When the radioactive dose according to experiment B is held back for a relevant holding time in order to arrive at certain radioactivity level before being delivered into a recipient or a patient for scanning purpose, the radioactivity concentration will become increasingly uneven as mixing, osmotic and diffusion effects will spread out the activity over an increasing length of tube. This corresponds to the theoretical decay graphs shown in FIG. 7.

The invention claimed is:

1. A method for preparing and delivering a bolus comprising the following steps:
   a. Providing a source of a radioactive solution of a radiopharmaceutical having a radioactive half-life of less than 21 minutes,
   b. providing a first valve having a waste position and a recipient position,
   c. providing a bolus conduit, a waste conduit and a recipient conduit, each conduit having a valve end being connected to said first valve, so that the first valve can establish a waste flow path in the waste position and a recipient flow path in the recipient position, the recipient flow path being different from said waste flow path, the bolus conduit comprising a measuring section and an internal volume, the internal volume being approximately equal to a selected volume of the radioactive solution to be delivered to a recipient,
d. arranging said first valve in the waste position,
e. transporting a first amount of said radioactive solution through said waste flow path, the first amount of said radioactive solution having an initial level of radioactivity that is at least approximately equal to or higher than a selected level of radioactivity and a volume that is larger than the internal volume of said bolus conduit,
f. providing a radiation detector, the radiation detector being operable to measure a level of radioactivity of the radioactive solution in said measuring section,
g. measuring a reference level of radioactivity of said radioactive solution present in said measuring section, characterized in that when the reference level of radioactivity is approximately equal to a predetermined injection level of radioactivity, the method further comprises the steps of:
h. arranging the first valve in the recipient position, and
i. transporting the radioactive solution present in the bolus conduit through the recipient flow path;
wherein the bolus is for non-surgical, non-therapeutic intravenous (IV) administration, the bolus comprising the radioactive solution of a radiopharmaceutical having a radioactive half-life of less than 21 minutes, said bolus having a substantially cylindrical body or delimitation and an unvarying radioactivity profile throughout the volume of the bolus.

2. The method according to claim 1, wherein the radiopharmaceutical is radioactive water.

3. The method of claim 2, wherein the radioactive water is 0-15 $H_2O$ or O14 $H_2O$.

4. The method according to claim 1, wherein the delivered bolus is in the range of 0.05-50 ml.

5. The method according to claim 1, wherein the injection speed is approximately 0.05-7 ml/sec.

6. The method according to claim 1, wherein the delivered bolus contains a delivered radioactivity (D) of 5 MBq up to 5.000 MBq.

* * * * *